United States Patent [19]

Wolfram et al.

[11] Patent Number: 5,454,841
[45] Date of Patent: Oct. 3, 1995

[54] COMPOSITIONS AND METHOD FOR TEMPORARILY COLORING HAIR USING A COMPLEX OF WATER SOLUBLE MELANIN AND A CATIONIC MATERIAL

[75] Inventors: L. Wolfram, Stamford; G. Wenke, Woodbridge, both of Conn.

[73] Assignee: Clairol, Inc., New York, N.Y.

[21] Appl. No.: 214,062

[22] Filed: Mar. 15, 1994

Related U.S. Application Data

[63] Continuation of Ser. No. 978,561, Nov. 19, 1992, abandoned.

[51] Int. Cl.⁶ ........................................... A61K 7/13
[52] U.S. Cl. ................ 8/405; 8/406; 8/554; 424/70.6
[58] Field of Search ........................... 8/405, 406, 423, 8/435, 554; 424/70, 70.1, 70.6

[56] References Cited

U.S. PATENT DOCUMENTS

| | | | |
|---|---|---|---|
| 3,993,436 | 11/1976 | Fujinuma | 8/423 |
| 4,453,941 | 6/1984 | Jacobs | 8/405 |
| 4,968,497 | 11/1990 | Wolfram et al. | 8/408 |
| 5,006,331 | 4/1991 | Gaskin | 424/70 |
| 5,216,116 | 6/1993 | Pawelek | 528/207 |
| 5,218,079 | 6/1993 | Pawelek et al. | 528/206 |
| 5,225,435 | 6/1993 | Pawelek et al. | 514/415 |

Primary Examiner—Linda Skaling Therkorn
Assistant Examiner—Caroline L. Dusheck
Attorney, Agent, or Firm—Anthony M. Santini

[57] ABSTRACT

Compositions comprising chemically synthesized or biosynthetic water-soluble melanin and at least one water dispersible cationic material which, when combined with the melanin, forms a composition that is suitable for use as a temporary haircolor. A process for temporarily coloring hair using those compositions.

8 Claims, No Drawings

COMPOSITIONS AND METHOD FOR TEMPORARILY COLORING HAIR USING A COMPLEX OF WATER SOLUBLE MELANIN AND A CATIONIC MATERIAL

This application is a continuation of application Ser. No. 978,561, filed Nov. 19, 1992, now abandoned.

BACKGROUND OF THE INVENTION

This invention relates to compositions and methods for temporarily coloring hair using chemically synthesized or giosynthetic water-soluble melanin.

Naturally-occurring melanin is the pigment that gives hair its color. A general discussion of the properties and chemistry of melanins may be found in Prota, G., "Progress In The Chemistry Of Melanins And Related Metabolites," *Med. Res. Reviews*, 8:525–56 (1988) and Moncrieff, R. W., *Manufacturing Chemist*, XXI, 8, 330–34 (August 1950). The gradual loss of melanin, with age, causes hair to turn gray.

Naturally-occurring melanin pigment itself is unacceptable for use in a hair dye composition because it is easily rubbed off the hair and leaves hair feeling rough. In the past, one of the best methods for coloring gray hair involved the use of naturally-occurring melanin precursors (such as 5,6 dihydroxyindole (DHI)) that when combined with an oxidant or a metal salt, form melanin pigments within the hair shaft. See, for example, U.S. Pat. No. 3,194,734 (Seemuller et al.), U.S. Pat. No. 4,808,190 (Grollier et al.), and U.S. Pat. No. 4,888,027 (Grollier et al.). However, the use of these melanin precursors has many disadvantages.

The primary disadvantage is that the haircolors initially produced with melanin precursors are undesirable achromatic colors (cold grays and blacks). Melanin precursor dyed hair must undergo a second treatment step with an oxidant such as hydrogen peroxide to achieve natural chromatic colors (warm yellows, reds, and browns). See, for example, U.S. Pat. No. 3,194,734 (Seemuller et al.). In addition, melanin precursors are expensive and, because they are highly reactive, difficult to work with. The use of melanin precursors also results in undesirable scalp and skin staining.

Furthermore, because melanin precursors penetrate the hair shaft, the haircolors produced using melanin precursors are permanent haircolors. That is, the haircolor must grow out with the hair. Often, consumers prefer to use a temporary haircolor that will wash out after one or two shampoos. However, temporary haircolors are unacceptable to consumers unless they do not fade in sunlight any more than natural haircolor, do not rub off, and do not bleed when in contact with perspiration, rain, or swimming pool water.

Therefore, there exists a need in the art for a composition that produces, in a single treatment step, temporary natural-looking haircolor that will not fade substantially in sunlight, will not rub off, and will not bleed when in contact with water; is inexpensive; will not stain skin; and is simple to work with. Applicants have surprisingly found an aqueous composition, which comprises chemically synthesized or biosynthetic water-soluble melanin and at least one water dispersible cationic material, that has each of those characteristics.

SUMMARY OF THE INVENTION

It is an object of this invention to provide a composition for temporarily coloring hair using chemically synthesized or biosynthetic water-soluble melanin.

It is also an object of this invention to provide a composition that will produce a temporary natural-looking hair color that will not fade in sunlight any more than natural haircolor, will not rub off, and will not bleed when in contact with water.

It is further an object of this invention to provide an inexpensive composition for temporarily coloring hair using chemically synthesized or biosynthetic water-soluble melanin.

It is also an object of this invention to provide a composition for temporarily coloring hair that comprises chemically synthesized or biosynthetic water-soluble melanin and will not stain skin.

It is also an object of this invention to provide a composition that is simple to work with for temporarily coloring hair using chemically synthesized or biosynthetic water-soluble melanin.

It is also an object of this invention to provide a one step process for temporarily coloring hair using chemically synthesized or biosynthetic water-soluble melanin.

In accordance with this invention, an aqueous composition is provided, for temporarily coloring hair, comprising chemically synthesized or biosynthetic water-soluble melanin and at least one water dispersible cationic material. A process for temporarily coloring hair, using that composition, is also provided.

DETAILED DESCRIPTION OF THE INVENTION

The present invention provides an aqueous composition comprising chemically synthesized or biosynthetic water-soluble melanin and at least one water dispersible cationic material which, when combined with the melanin, forms a composition that is suitable for use as a temporary haircolor. The chemically synthesized or biosynthetic water-soluble melanins that are suitable for use with this invention must have an anionic character and should be capable of forming a complex with the water dispersible cationic material.

The amount of melanin required in the composition of this invention will vary according to factors such as the carrier used, the starting haircolor, and the desired end haircolor. Thus, a tinctorially effective amount of melanin should be used. In general, however, the amount of melanin required will be about 0.1% to about 5.0%, preferably the amount of solubilized melanin will be about 0.2% to about 5.0%.

The water dispersible cationic materials that may be used in the present invention must, when combined with the melanin, be capable of forming a composition that is suitable for use as a temporary haircolor. That is, the mixture of cationic materials and water-soluble melanin must be either water-soluble or water-dispersible under the conditions at which they will be used. Preferably, the cationic materials and water-soluble melanin will form a stable homogenous solution or emulsion. These water dispersible cationic materials will also form a complex with water-soluble anionic melanins. Such water dispersible cationic materials include cationic surface active agents, cationic surfactants, cationic polymers, and salts thereof. Materials that assume a cationic character at a certain pH are also water dispersible cationic materials in accordance with this invention. Specific water dispersible cationic materials that may be used include: dicetyldimonium chloride, Merquat 100, (poly dimethyl diallyl ammonium chloride) Merquat 3330 (an aqueous solution of a polyampholyte terpolymer consisting of acrylic acid, dimethyl diallyl ammonium chloride and acrylamide) and Polyquaternium-11 (a quaternary ammonium polymer formed by the reaction of dimethyl sulfate and a copolymer of vinyl pyrrolidone and dimethyl aminoethylmethacrylate). The water dispersible cationic materials are preferably present in amounts sufficient to form a complex with substantially all of the melanin in the composition. The ratio of melanin to water dispersible cationic material that is useful in the composition of this invention varies widely. However, in general, the ratio will be from about 1:4 to about 10:1.

The composition of this invention is stable over time. That is, hair can be temporarily dyed immediately after the melanin is combined with the water dispersible cationic material, or application of the composition can be delayed.

Although the pH of the composition may not be so low or high as to damage hair, the composition is useful at a wide range of pH values. The correct pH for a particular composition is a function of the type of water dispersible cationic material used and the amount of melanin. In general, however, the pH of the composition will be about 4 to about 8.

In addition to melanin and water dispersible cationic material, it may be desirable to include cosmetically acceptable carriers in the compositions of this invention. Acceptable carriers vary from simple solutions or dispersions with aqueous or alcoholic solvents, to complex mixtures that contain thickening agents. The carriers that may be used in accordance with this invention must be compatible with chemically synthesized or biosynthetic water-soluble melanin.

It may also be desirable to include in the compositions of this invention adjuvants or additives that are commonly found in haircolor compositions, in amounts effective to provide their intended function. Such adjuvants or additives include solvents, solubilizing agents, thickening agents, alkalizing agents, chelating agents, preservatives and fragrances.

The solvents that may be used include organic solvents or solvent systems that are compatible with water-soluble melanin. A number of organic solvents are known in the art that are useful for such purposes. These organic solvents include alcohols, particularly alkyl alcohols of 1–6 carbons, especially ethanol and propanol; and glycols of up to about 10 carbons, especially diethyleneglycol, monobutyl ether, carbitols, and benzyl alcohol.

The thickening agents that may be used in the compositions of this invention include: polyvinylpyrrolidone, gum arabic, cellulose derivatives such as methylcellulose or hydroxyethylcellulose, and inorganic thickeners such as bentonite.

The additional solubilizing agents that may be used in the compositions of this invention include ethoxylated fatty alcohols.

The preservatives that may be used in the compositions of this invention include: methyl- and propyl paraben, 2-phenoxyethanol, DMDMH, and Kathon CG.

The haircolor compositions of this invention may be prepared by methods known in the art.

This invention also provides a process for temporarily coloring hair, which comprises applying to the hair an aqueous composition comprising chemically synthesized or biosynthetic water-soluble melanin and .at least one water disperable cationic material. The haircolor compositions may be applied to the hair by conventional techniques known in the art. For example, they can be poured over the hair or applied with an applicator. The amount of time for which the dye composition must be in contact with the hair is not critical. It may vary from about 2 minutes to about 50 minutes, but is usually from about 5 minutes to about 30 minutes.

It will be apparent to those skilled in the art that the invention described herein can be practiced by other than the embodiments disclosed herein, which are presented for the purposes of illustration and not of limitation, and the present invention is limited only by the claims that follow.

We claim:

1. A temporary hair coloring composition comprising about 0.1% to about 5.0% by weight of an anionic water-soluble melanin and at least one water-dispersible cationic material, wherein the ratio of said melanin to said cationic material is from about 1:4 to about 10:1, and wherein the melanin and the cationic material form a complex effective for temporarily coloring hair.

2. The composition of claim 1 wherein the cationic material is selected from the group consisting of cationic surface active agents, cationic surfactants, cationic polymers, and salts thereof.

3. The composition of claim 2 wherein the cationic material is selected from the group consisting of dicetyldimonium chloride; poly (dimethyl diallyl ammonium chloride); an aqueous solution of a polyampholyte terpolymer consisting of acrylic acid, dimethyl diallyl ammonium chloride and acrylamide; and a quaternary ammonium polymer formed by the reaction of dimethyl sulfate and a copolymer of vinyl pyrrolidone and dimethyl aminoethylmethacrylate.

4. The composition of claim 1 comprising a stable homogeneous solution or emulsion.

5. The composition of claim 1 further comprising an additive selected from the group consisting of cosmetically acceptable carriers, solvents, solubilizing agents, thickening agents, alkalizing agents, chelating agents, preservatives, fragrances and mixtures thereof.

6. A process for temporarily coloring hair comprising forming a complex comprising a tinctorially effective amount of an anionic water-soluble melanin and at least one water-dispersible cationic material, wherein the ratio of said melanin to said cationic material is from about 1:4 to about 10:1, and allowing the complex to be in contact with the hair for a period of time sufficient to temporarily dye the hair.

7. The process of claim 6 wherein said period of time is from about 2 minutes to about 50 minutes.

8. The process of claim 6 wherein said complex is applied to the hair in a single treatment step.

* * * * *